US012310883B2

(12) United States Patent
McMahon

(10) Patent No.: US 12,310,883 B2
(45) Date of Patent: May 27, 2025

(54) CONTINUOUS THERMAL THERAPY

(71) Applicant: Solana Health, Inc., Del Mar, CA (US)

(72) Inventor: David McMahon, Del Mar, CA (US)

(73) Assignee: OcuSci, Inc., Del Mar, CA (US)

( * ) Notice: Subject to any disclaimer, the term of this patent is extended or adjusted under 35 U.S.C. 154(b) by 447 days.

(21) Appl. No.: 17/871,857

(22) Filed: Jul. 22, 2022

(65) Prior Publication Data

US 2023/0021958 A1 Jan. 26, 2023

Related U.S. Application Data

(60) Provisional application No. 63/225,446, filed on Jul. 23, 2021.

(51) Int. Cl.
*A61F 7/00* (2006.01)

(52) U.S. Cl.
CPC ...... *A61F 7/007* (2013.01); *A61F 2007/0004* (2013.01); *A61F 2007/0078* (2013.01); *A61F 2007/0087* (2013.01)

(58) Field of Classification Search
CPC .............. A61F 2007/0004; A61F 7/007; A61F 2007/0078; A61F 2007/0087; A61F 2007/0088
See application file for complete search history.

(56) References Cited

U.S. PATENT DOCUMENTS

| | | |
|---|---|---|
| 4,308,013 A | 12/1981 | Major |
| 5,097,828 A | 3/1992 | Deutsch |
| D361,404 S | 8/1995 | Haas |
| 5,573,529 A | 11/1996 | Haak et al. |
| 5,618,274 A | 4/1997 | Rosenthal |
| 5,830,208 A | 11/1998 | Muller |
| 6,047,215 A | 4/2000 | McClure et al. |
| 6,436,113 B1 | 8/2002 | Burba et al. |
| 6,679,908 B2 | 1/2004 | Shimizu |
| 7,120,488 B2 | 10/2006 | Nova et al. |
| 7,231,922 B2 | 6/2007 | Davison et al. |
| 8,491,505 B2 | 7/2013 | Yang |
| 8,523,791 B2 | 9/2013 | Castel |
| 8,613,762 B2 | 12/2013 | Bledsoe |
| 8,721,572 B1 | 5/2014 | Linder et al. |
| 8,758,419 B1 | 6/2014 | Quisenberry et al. |
| 8,876,859 B2 | 11/2014 | Buehler et al. |
| D773,038 S | 11/2016 | Tanner et al. |

(Continued)

OTHER PUBLICATIONS

High Frequency Facial Wand Machine, first available Oct. 20, 2020, amazon.co.uk, [online], [site visited Sep. 20, 2024], Available from internet URL: https://www.amazon.co.uk/dp/B08LGVMVPX/ (Year: 2020).

(Continued)

*Primary Examiner* — Linda C Dvorak
*Assistant Examiner* — Bradford C. Blaise
(74) *Attorney, Agent, or Firm* — Batt IP A Law Corporation; Richard Batt

(57) ABSTRACT

A non-invasive thermal therapy for the eye dynamically maintains a treatment temperature at the working tip of the instrument. Methods described herein pre-heat the instruments serving to reduce instrument setup time, increase battery life, reduce the weight of the handheld device, and reduce total procedure time. Related apparatuses are also described.

20 Claims, 4 Drawing Sheets

(56) References Cited

U.S. PATENT DOCUMENTS

| | | |
|---|---|---|
| 9,763,827 B2 | 9/2017 | Kelleher et al. |
| 9,956,355 B2 | 5/2018 | Besirli et al. |
| 10,130,507 B2 | 11/2018 | Whitehurst et al. |
| 11,517,473 B2 | 12/2022 | McMahon |
| D1,010,810 S | 1/2024 | He |
| D1,016,305 S | 2/2024 | Wang |
| 12,102,561 B2 | 10/2024 | McMahon |
| 2001/0007952 A1 | 7/2001 | Shimizu |
| 2001/0042743 A1* | 11/2001 | Faries, Jr. ............ A61M 5/445 219/400 |
| 2002/0087179 A1 | 7/2002 | Culp et al. |
| 2004/0068309 A1 | 4/2004 | Edelman |
| 2007/0060988 A1 | 3/2007 | Grenon et al. |
| 2008/0046047 A1 | 2/2008 | Jacobs |
| 2008/0046048 A1 | 2/2008 | Grenon et al. |
| 2008/0109052 A1 | 5/2008 | Grenon et al. |
| 2008/0109053 A1 | 5/2008 | Grenon et al. |
| 2008/0228248 A1 | 9/2008 | Guyuron et al. |
| 2010/0016933 A1 | 1/2010 | Chen et al. |
| 2012/0016275 A1 | 1/2012 | Korb et al. |
| 2012/0165908 A1 | 6/2012 | Kou et al. |
| 2012/0209154 A1 | 8/2012 | Williams, III et al. |
| 2012/0239122 A1 | 9/2012 | Dong et al. |
| 2013/0085552 A1 | 4/2013 | Mandel |
| 2013/0116719 A1 | 5/2013 | Shtram et al. |
| 2013/0184693 A1 | 7/2013 | Neev |
| 2013/0281851 A1 | 10/2013 | Carr |
| 2014/0200487 A1 | 7/2014 | Ramdas et al. |
| 2014/0231406 A1* | 8/2014 | Tsang ............ A61M 5/44 219/394 |
| 2014/0249455 A1 | 9/2014 | Parish et al. |
| 2015/0005750 A1 | 1/2015 | Kelleher et al. |
| 2015/0032059 A1 | 1/2015 | Allerdings et al. |
| 2015/0051545 A1 | 2/2015 | Henderson et al. |
| 2015/0056095 A1 | 2/2015 | Gorzen et al. |
| 2015/0057701 A1 | 2/2015 | Kelleher et al. |
| 2015/0157190 A1* | 6/2015 | Temple ............ A61B 1/127 219/429 |
| 2015/0157347 A1 | 6/2015 | Grenon et al. |
| 2015/0157530 A1 | 6/2015 | Sanchez Soriano |
| 2015/0216722 A1 | 8/2015 | Choate |
| 2015/0216725 A1* | 8/2015 | Korb ............ A61F 9/00718 606/171 |
| 2015/0272623 A1 | 10/2015 | Ignon et al. |
| 2015/0283402 A1 | 10/2015 | Grenon et al. |
| 2015/0320590 A1 | 11/2015 | Whitehurst et al. |
| 2015/0366703 A1 | 12/2015 | Du |
| 2016/0243000 A1 | 8/2016 | Gray |
| 2016/0317379 A1 | 11/2016 | Mosaddegh |
| 2017/0087009 A1 | 3/2017 | Badawi et al. |
| 2017/0273823 A1* | 9/2017 | Novkov ............ A61F 7/02 |
| 2019/0060115 A1* | 2/2019 | Novkov ............ A61H 15/02 |
| 2019/0307606 A1 | 10/2019 | Andino et al. |
| 2020/0069468 A1 | 3/2020 | Litherland et al. |
| 2020/0188169 A1* | 6/2020 | McMahon ............ A61F 7/00 |

OTHER PUBLICATIONS

PCT/US2018/048001 Written Opinion ISR, Oct. 22, 2018.
Resin Heater User Manual 2020.
The Nu lids Starter Kit—Nulids at-Home Dry Eye Treatment and Relief, first available Nov. 22, 2019, amazon.co.uk, [online], [site visited Sep. 20, 2024], Available from internet URL: https://www.amazon.co.uk/NuLids-Starter-Kit-Convenient-Blepharitis/dp/B08247ZVLB?th=1 (Year: 2019).

* cited by examiner

CONTINUOUS THERMAL THERAPY

CROSS-REFERENCE TO RELATED APPLICATIONS

This application claims priority to provisional application No. 63/225,446, filed Jul. 23, 2021, and entitled "Continuous Thermal Therapy".

BACKGROUND OF THE INVENTION

1. Field of the Invention

The subject matter of the present disclosure is directed to thermal therapy, and particularly, to thermal therapy related to the eyelid.

2. Description of the Related Art

The leading causes of dry eyes are Blepharitis, in particular Posterior Blepharitis and dysfunction of the meibomian glands, also known as Meibomian Gland Dysfunction (MGD).

Blepharitis is defined as inflammation of the eyelids. Posterior Blepharitis involves inflammation of the Meibomian Glands and is marked by oily, gritty, or foamy discharge from the Meibomian Glands.

Blepharitis most commonly occurs when tiny oil glands (namely, the meibomian glands) located on the posterior edge of the lid margin are inflamed and become clogged. This leads to irritated and red eyes. Blepharitis is often a chronic condition that is difficult to treat. Blepharitis can be uncomfortable and may be unsightly.

MGD is when blockage or some other abnormality of the meibomian glands in the lower and upper eyelids prevent secretion of meibum to the surface of the eye. Although MGD can include cases of either hypersecretion of meibum or hyposecretion, most cases of MGD and blepharitis involve blockage and obstruction of the meibomian glands, with associated decreased secretion of meibum.

This is undesirable because meibum is a key component to keep the lipid tear layer in contact with the surface of the eye and its absence leads to inappropriate evaporation of tears from the eye surface and hence dry eye results.

One approach to treating MGD is eyelid hygiene. Typically, care includes eyelid massage, often after applying heat or warm compresses, and then attempting to clean the eyelid with mild soaps. If this is ineffective, artificial tears, lubricants, antibiotics, anti-inflammatories, lipid diet supplements, cyclosporine may be prescribed.

In addition to eyelid hygiene, a number of thermal therapy devices exist for treating MGD including the MiBo Thermoflo device manufactured by MIBO Medical Group (Dallas, Texas) and the LipiFlow Thermal Pulsation System manufactured by Johnson & Johnson (Morrisville, North Carolina).

However, each of the above-mentioned thermal therapy devices applies only one treatment modality. Particularly, the MiBo Thermoflo device applies only heated massage and the LipiFlow Thermal Pulsation System applies only thermal pulsation.

Accordingly, there is a need for improved systems that address the above challenges.

SUMMARY OF THE INVENTION

In embodiments of the invention, a non-invasive eyelid treatment method comprises providing a plurality of different types of thermal treatment instruments. Each type of instrument has a common or identically-shaped base portion and a unique distal working end. A battery-powered handheld device is provided that is adapted to detachably engage the base portion of each type of thermal therapy instrument. The handheld device is also adapted to dynamically control heat to the distal working end through thermal conduction. The method further comprises pre-heating the thermal therapy instruments.

A first type of pre-heated instrument is installed in the handheld device; and a corresponding first thermal therapy is performed on the eyelid using the first pre-heated thermal therapy instrument. Then, without charging the handheld device, the first instrument is exchanged for a preheated second type of instrument. The second thermal therapy is performed using the second instrument installed in the handheld device.

The process is continuously repeated, exchanging a pre-heated thermal therapy instrument for the previously-installed instrument until several thermal therapies, optionally different types, are performed on the patient without charging the handheld device.

In embodiments, the thermal therapy instruments are pre-heated to a target or precursor temperature ranging from 45-50 degrees C., and preferably about 47-49 degrees C.

In embodiments, pre-heating is performed by an electric heater including a plurality of heated ports.

In embodiments, a portable thermally conductive tubular insert is sized to fit in a heater port. The insert comprises a hole for receiving the base portion of the thermal therapy instrument. When the heater is turned on, heat is transferred from the port, through the insert and to the instrument.

In embodiments, each port is fitted with an insert to receive an instrument base portion.

In embodiments, the hole in the insert is key-shaped. This serves to provide a snug, rotation-less fit between the instrument and the insert, thereby improving thermal conductivity.

In embodiments, the heater comprises 1 to 15 ports, and more preferably 5-10 ports. The heater is operable to heat each port in parallel.

In embodiments, the plurality of types of thermal therapy instruments include a massage instrument having an atraumatic planar face, a debriding instrument having a hockey stick-shaped tip, and an expression instrument with pivotable jaws for clamping the eyelid.

In embodiments, the handheld device comprises a small lightweight battery, preferably a lithium-ion battery.

In embodiments, in a method for performing therapy on the eye using a dynamically-thermally controlled handheld therapy device to adjust temperature during treatment, an improvement comprises pre-heating a plurality instruments prior to installing each of the instruments in the handheld device.

In embodiments, the first type of thermal therapy instrument is a massage instrument, and the second type of thermal therapy instrument is one type selected from the group comprising a debriding instrument and an expression instrument.

In embodiments, the performing steps by each of the first, second, and third type of thermal therapy instruments are at least 2-6 minutes, optionally at least 5 minutes, and wherein the handheld device maintains each of the working ends of the instruments at a treatment temperature of at least 40 degrees C. In embodiments, a heater assembly for thermal therapy comprises a table-top electric heater comprising a plurality of ports, and a plurality of inserts shaped to individually engage with each of the ports. Each insert comprises a cavity having a key-shaped cross section to receive a keyed-base portion of a plurality of different types of heatable instruments.

In embodiments, a tubular-shaped insert comprises an exterior surface adapted to fit in a heater port and to maintain thermal contact with the port. The insert comprises a cavity having a key-shaped cross section to receive a keyed-base portion of a plurality of different types of heatable instruments. Optionally, the insert comprises an upper flange that acts as a stop as the insert is inserted into the heater port. The stop contacts an exterior face of the heater.

In embodiments, the handheld device is small and light such that it can be used comfortably on delicate tissue such as, e.g., the eyelid.

In embodiments, the handheld device is cordless, i.e., does not require a power cord despite being an actively-thermally controlled therapy device. Thus, a heavy battery or an AC power cord are not able to be used—that is the value of the pre-heater.

In embodiments, in a method for performing thermal therapy on the eyelid using a dynamically-thermally controlled handheld therapy device to adjust temperature during treatment, an improvement comprises pre-heating a plurality instruments prior to installing one of said instruments in the handheld device.

In embodiments, a heater assembly for thermal therapy comprises a table-top electric heater comprising a plurality of ports, and a plurality of inserts shaped to engage with each of the ports, wherein each insert is adapted to receive a universal base portion of a plurality of different types of heatable instruments. In embodiments, each insert comprises a cavity having a key-shaped cross section to receive a keyed-base portion of the plurality of different types of heatable instruments.

In embodiments, a tubular-shaped insert comprises an exterior surface adapted to fit in a heater port and to maintain thermal contact with the port. In embodiments, the insert comprises a cavity having a key-shaped cross section to receive a keyed-base portion of a plurality of different types of heatable instruments. In embodiments, the insert comprises an upper flange that contacts an exterior face of the heater, preventing the insert from further penetration into the port.

OBJECTS AND ADVANTAGES OF THE INVENTION

Preheating instruments for thermal therapy has a number of advantages including: minimizing waiting time for the instrument to warm to a therapeutically adequate temperature, minimizing overall procedure time, and maximizing the battery life of the handheld device because no power is required to warmup the thermal therapy instrument. This is especially beneficial for heating instruments that dynamically control the temperature (e.g., maintain a set temperature at the tip during the procedure based on monitoring temperature and adjusting the power to the instrument based on the monitored temperature). Dynamically controlling the temperature requires more power—the system thus cannot afford to waste power during warmup. The subject invention addresses these challenges.

The description, objects and advantages of embodiments of the present invention will become apparent from the detailed description to follow, together with the accompanying drawings.

DETAILED DESCRIPTION OF THE INVENTION

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described. It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order that is logically possible.

All existing subject matter mentioned herein (e.g., publications, patents, patent applications and hardware) is incorporated by reference herein in its entirety except insofar as the subject matter may conflict with that of the present invention (in which case what is present herein shall prevail). Each of the following are incorporated herein by reference in their entirety for all purposes: US patent publications nos. 20200188169; 20190060115; and 20170273823.

Figure 1:
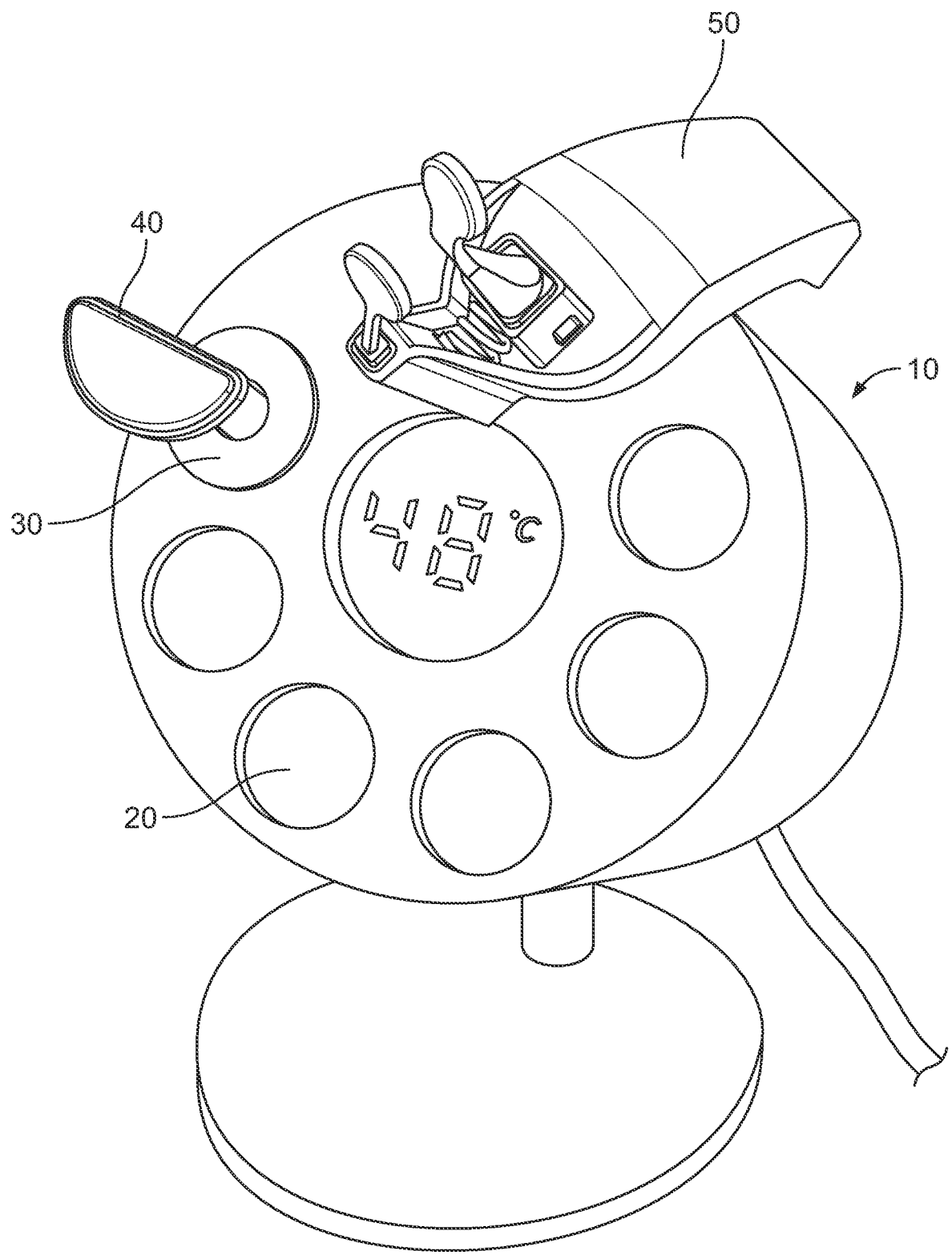
FIG. 1 is a perspective view of a heater assembly in accordance with an embodiment of the invention.

FIG. 1 depicts a table-top sized instrument heater 10 for pre-heating various different types of thermal eye-therapy instruments 40, 50 in accordance with an embodiment of the invention. Examples of suitable instruments are described in, e.g., US patent publications no. 20200188169 to McMahon.

The instrument heater 10 is shown having a planar exterior face defining a plurality of universal or identically-shaped ports 20 in which a custom heater insert 30 may be received. As discussed herein, the insert 30 is configured to accept the various instruments (e.g., 40, 50) for pre-warming.

A number of components of the heater are typical components found in conventional heaters. For example, and not shown, the heater 10 can include a heating element, power cord, user interface, and electronics to controllably warm each port or socket by thermal conduction or electrical resistive heating. Consequently, when the insert/instrument assembly is registered in the socket 20, as shown in FIG. 1 with reference to instruments 40, 50, and the heater is activated, each insert/instrument assembly is warmed.

The heater shown in FIG. 1 also includes a display indicating the temperature. The target or set temperature may be dialed in via the user interface (e.g., touchscreen, buttons, or knobs). Optionally, the heater may include a communication module to communicate with a user. In embodiments, the communication module is wireless, preferably, operable in the near field spectrum. In a preferred embodiment, the communication module is Bluetooth compatible. An example of an electric heater is the Dental Composite Heater by TREE INTERNATIONAL TRADING COMPANY LIMITED (China).

In embodiments, after the temperature is set by the user, the set temperature is shown in the center digital display. In embodiments, the set temperature is set to 50 degrees Celsius to pre-heat the instruments such that the instruments are pre-heated to a pre-cursor temperature between 44-47 degrees Celsius, even though the temperatures required for treatments (namely, treatment temperature) are between 40-42 degrees Celsius. This novel over-heating step is done purposefully to mitigate the temperature loss arising from the time to remove the instruments from the pre-heater and place them in the dynamic handheld heating device. We have seen temperature losses from 4-8 degrees Celsius or more, depending on ambient room temperature, etc. Additionally, this method of overheating the instruments in the pre-heating phase of the process has demonstrated to be a very time-efficient method of enabling the user to switch instruments, resulting in switch times of 30-40 seconds. The heater may also be programmed and operable to show the instant temperature in a blinking or otherwise indicate the set temperature has not been reached. In embodiments, a speaker can emit an audible signal once the instant temperature reaches the set temperature.

Figure 2A:
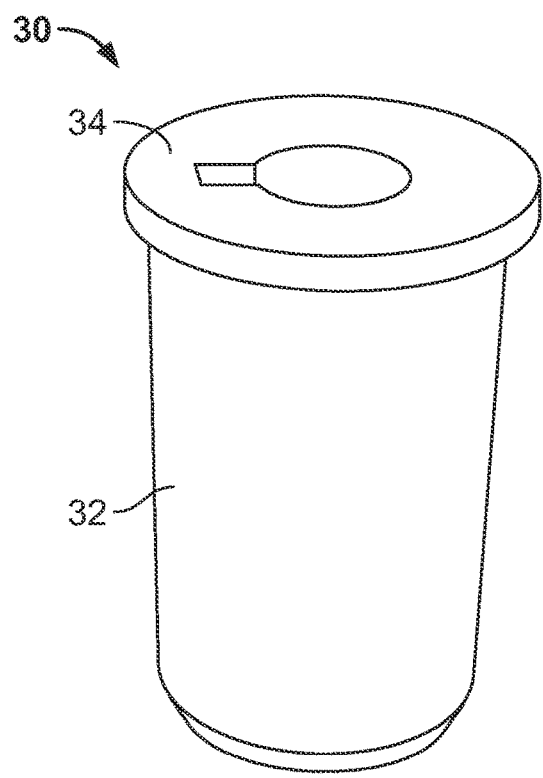
FIG. 2A is a top side perspective view of a heater insert in accordance with an embodiment of the invention.
Figure 2B:
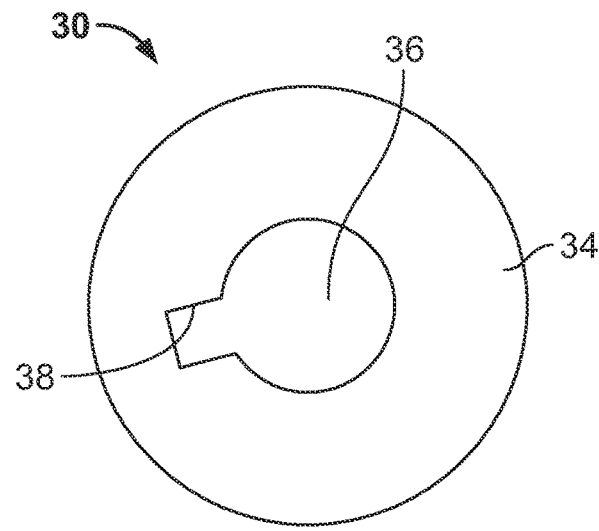
FIG. 2B is a top view of the heater insert shown in FIG. 2A.
Figure 2C:
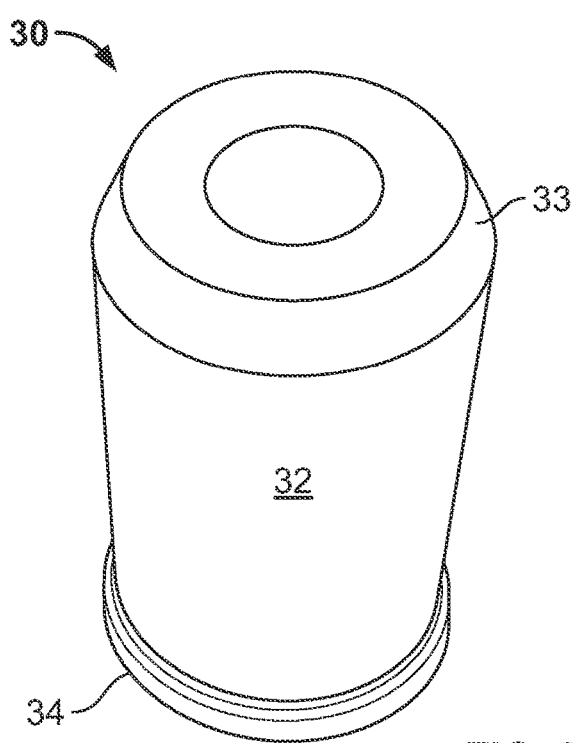
FIG. 2C is a bottom side perspective view of the heater insert shown in FIG. 2A.

FIGS. 2A-2C depict various views of a heater insert 30 in accordance with embodiments of the invention. The insert 30 includes a body 32, and rim or flange 34 which engages the planar face of the heater 10. The insert 30 also shows a hole 36 and slot 38 collectively forming a key hole for receiving the instrument shaft 42, 52, 62 and key 44, 54, 64, discussed herein. This custom interface serves to reliably align and maximize thermal conductivity between the instrument (e.g., 40, 50, or 60) and the instrument heater 10.

With reference to FIG. 2C, a bottom perspective view of the insert 30 is shown. The bottom end of the body 32 is shown having taper 33, bottom face, and bottom hole. The taper facilitates insertion of the insert into the ports 20 of the heater. Not shown, a contiguous lumen extends from the bottom hole to the upper hole 36 in which the base portion of the instrument is received as described above. Typically, the insert is fabricated from rigid thermally conducting materials such as steel or an alloy. In embodiments, the insert is stainless steel or aluminum.

Figure 3:
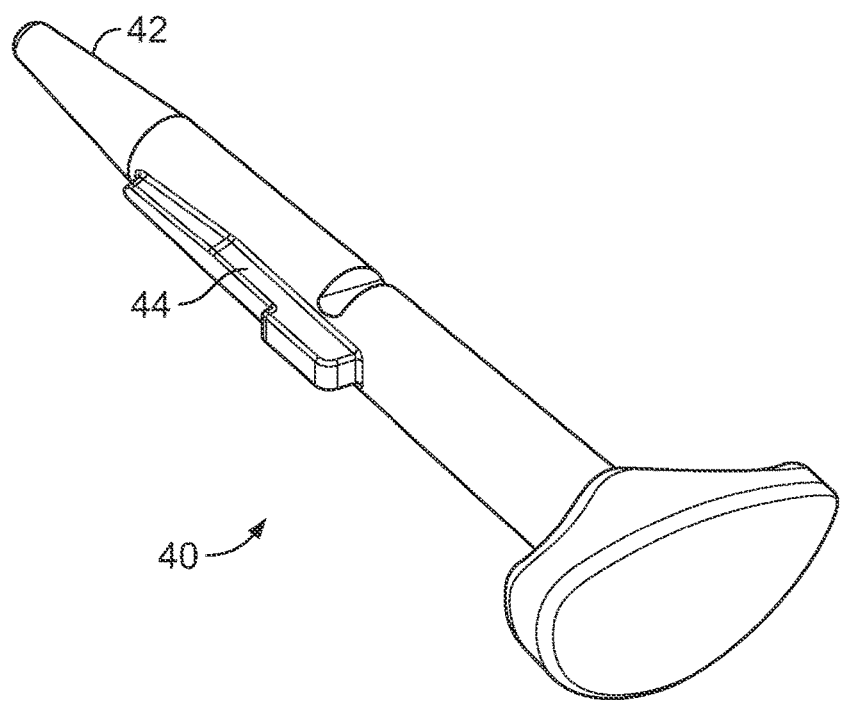
FIGS. 3-5 are perspective views of different thermal therapy instruments in accordance with embodiments of the invention.
Figure 4:
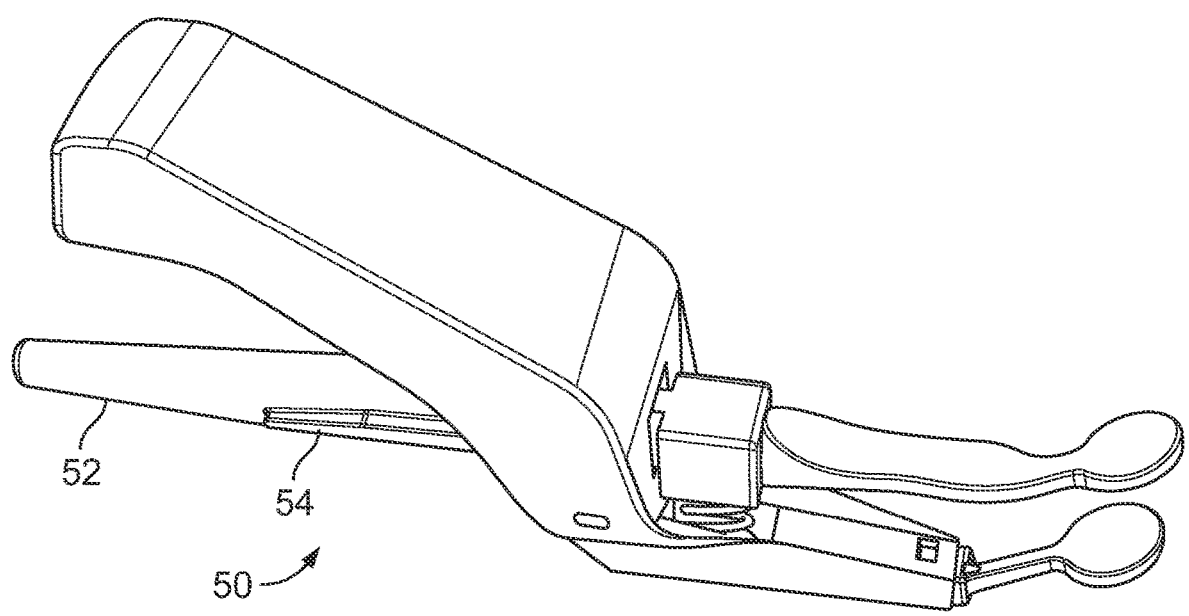
Figure 5:
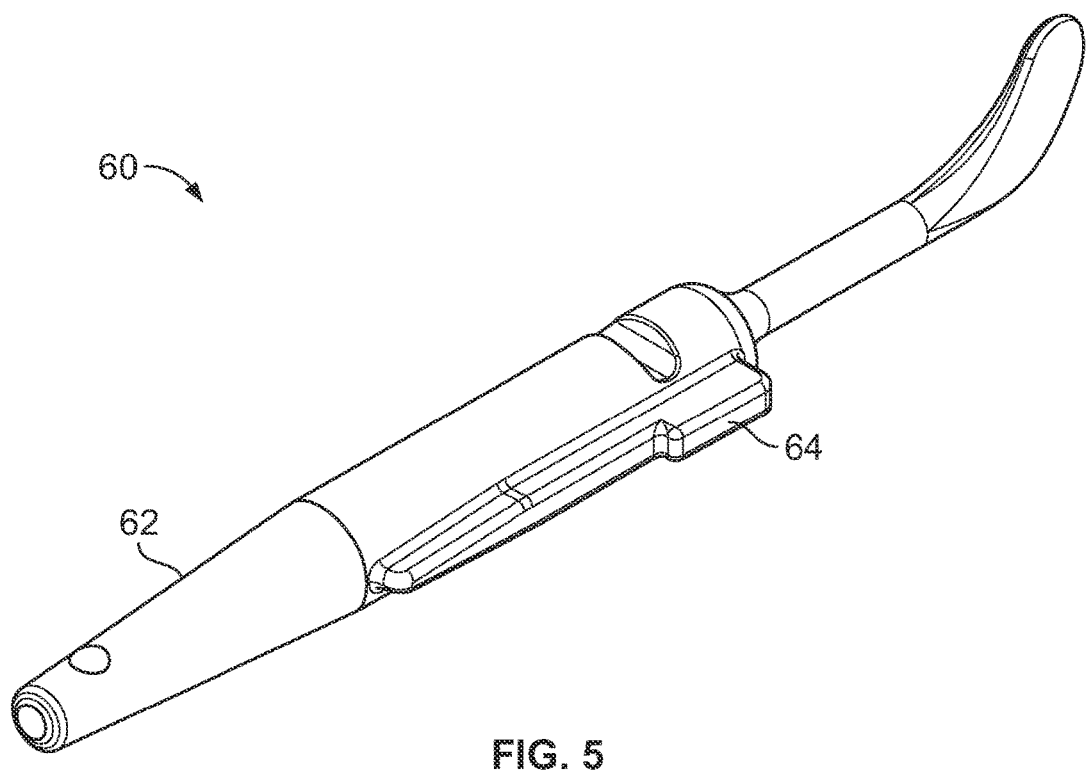

FIGS. 3-5 depict different types of thermal therapy instruments 40, 50, and 60 for use in the subject invention including massage instrument 40, expression instrument 50, and debriding instrument 60, respectively.

Each type of instrument is shown comprising a unique distal working end for contacting or operating on the eyelid and a common or identical base portion. The common base portion includes a tapering proximal end 42, 52, and 62, and a key 44, 54, and 64 which cooperate with the insert described above. The base portion can be advanced into the keyed hole in the insert. The insert hole and base portion are sized to make contact with one another so as to efficiently conduct heat between one another. Good contact is desired because the insert warms the instrument by thermal conduction.

Figure 6:
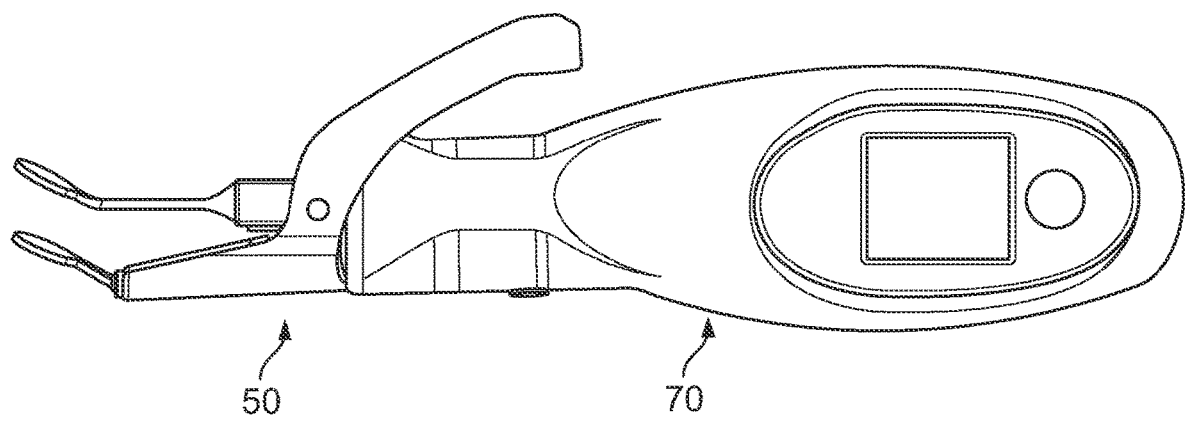
FIG. 6 is a handheld thermal treatment device in functional engagement with the instrument shown in FIG. 4 in accordance with an embodiment of the invention.

FIG. 6 illustrates a thermal battery-operated handheld therapy device 70 having installed therein an expression instrument 50. The handheld therapy device includes an internal socket adapted to lockingly engage the base portion of the instrument 50. The handheld therapy device 70 is operable to transmit heat to the instrument, and particularly, to dynamically control the temperature of the working end of the expression instrument based on a temperature feedback loop and control algorithm. Examples of the thermal therapy handheld instruments are described in US Patent Publication No. 20200188169 to McMahon.

Notably, the handheld device 70 shown in FIG. 6 is portable, batter-operated, cordless, and lightweight, providing the advantage of allowing the operator to manipulate the eyelid without requiring a bulky heavy instrument or the inconvenience of a cord that can cause snagging or otherwise impede the free movement of the device in the clinician's hand. The small lightweight device 70 provides more tactile feedback to the operator, tends to be gentler on the patient, and is more conveniently handled by the operator. In embodiments, the thermal therapy handheld device weighs between 3 to 5 ounces.

A challenge that arises, however, when using such small lightweight designs is power drain because of the need to dynamically control temperature. When a fresh instrument is installed in the handheld device, the handheld device must warm the instrument to the desired treatment temperature. In treatment rooms (which are typically kept colder than standard room temperature or around 68 degrees Fahrenheit), the instrument must be warmed to upwards of 42 degrees C. or higher. This takes 3-5 minutes and drains the battery before the treatment has even commenced.

Such conventional techniques limit a treatment to only one patient and then require at least 30 minutes of charge time for the handheld device to replenish its battery. In contrast, utilizing the pre-heating method in accordance with embodiments of the invention, a clinician is able to treat at least three patients in a row without charging the battery of the handheld device. The new therapy methods described herein serve to address this undesirable but typical shortcoming associated with the conventional devices.

Method of Treatment

A method for thermally treating tissue in accordance with one embodiment of the invention comprises inserting one or more inserts (e.g., inserts 30) into the ports 20 of the heater instrument 10. Preferably, a plurality of inserts are loaded into the empty ports 20 of heater 10.

Next, one or more instruments are inserted into empty inserts. This step may be repeated until each of the available inserts has received an instrument. Preferably, a plurality of different types of instruments (e.g., 40, 50, 60) are loaded into the available inserts 30.

Next, the instrument heater 10 is set to a pre-cursor or target temperature, preferably above desired treatment temperature by a predetermined delta T. In embodiments, the delta T ranges from 5-10 degrees, and more preferably 4-6 degrees above the desired treatment temperature. In embodiments, a temperature range is selected that (a) minimizes heating time and (b) maximizes battery life (and usage) of the handheld battery-operated treatment device 70. In an exemplary therapy application, the handheld battery-operated treatment device operates in a in a treatment mode to heat (and dynamically maintain) the instruments (e.g., 40, 50, 60) in a temperature range of 42-44° C. In embodiments, exemplary pre-cursor target temperatures for the heater are 45-50° C., more preferably, 47-49° C., and in some embodiments about 48° C.

Next, and if an instrument is already present in the handheld device, the user exchanges (replaces, or swaps) the previously installed instrument from the handheld treatment device 70 for the pre-warmed instrument in the heater 10, without charging the battery. The pre-warmed instrument enables efficient mode changes (~30 seconds per switch vs. 3 minutes or more without the pre-heating step) due to the lead time to warm a room temperature instrument. Without efficiently pre-heating the instruments in the heater 10 as described herein, the instruments 40, 50, 60 must be warmed/heated in the therapy treatment device itself (e.g., 70) prior to commencing therapy. This can take 2-3 minutes or more while the patient and operator wait. Battery power is also wasted during this "warm-up" period.

Next, treatment is performed using the freshly installed instrument in the handheld therapy device. In embodiments, substantially continuous treatment procedure times of 15-17 minutes (versus 22-25 minutes without pre-heating) are supported via use of the pre-heating step in accordance with the subject intention.

As mentioned herein, an advantage of the subject invention is the lightweight portable nature of the handheld device, enabled by pre-warming the instruments.

In contrast, if the instruments were required to be warmed in the handheld device itself, and in combination with the handheld dynamically maintaining a set treatment-mode temperature, the battery would be quickly drained. This problem is compounded when it is desired to perform several treatments continuously in sequence on a patient.

An alternative, as mentioned above is to provide power to the handheld device via a power cord which is also undesirably. Power cords and the associated electronics are cumbersome, increase the weight, and creates an obstacle (namely, the bulky cord) to deal with during the procedure.

Alternative Embodiments

While a number of embodiments and variations thereof have been described in detail, other modifications and methods of using the same will be apparent to those of skill in the art. For example, the shape of the hole in the insert may be adapted to the shape of other thermal therapy instruments. In alternative embodiments, the insert hole is a circle, oval, square, triangle, or other shape. The hole may include more or less slots (or features) to mate with cooperating features on the base portion of the instrument.

Additionally, although the handheld therapy device has been described in connection with treating the eyelid and eye, the subject invention may be applied to other anatomies and applications where pre-warming would be an advantage or benefit.

Additionally, although three types of thermal therapy instruments were described above, the subject inventions can include additional types of thermal therapy instruments.

Additionally, the number of ports, instruments, inserts, may vary widely.

Additionally, embodiments can include various operations as set forth above, fewer operations, or more operations; or operations in another order than that specifically described above.

Additionally, any of the components and steps described herein may be combined with one another in any logical manner except where such components or steps would be exclusive to one another.

Accordingly, the scope and spirit of the invention should be judged in terms of the claims, which follow as well as the legal equivalents thereof.

The invention claimed is:

1. A non-invasive thermal-based eyelid treatment method comprising:
   (a) providing a plurality of types of thermal therapy instruments having an identically-shaped base portion, and wherein each type of thermal therapy instrument comprises a unique distal working end;
   (b) providing a battery-powered handheld device, the handheld device comprising a handle and a distal socket adapted to detachably engage the base portion of each type of thermal therapy instrument, and adapted to dynamically control heat to the distal working end of each thermal therapy instrument through thermal conduction;
   (c) pre-heating the plurality of thermal therapy instruments, wherein the pre-heating is performed by an electric heater including a plurality of heated ports, wherein a thermally conductive insert is arranged in one of said plurality of heated ports, and wherein the thermally conductive insert comprises a hole for receiving and engaging the base portion of the thermal therapy instrument, and during the pre-heating step, heat is transferred from the port, through the insert and to the thermal therapy instrument;
   (d) installing a first type of pre-heated thermal therapy instrument in the handheld device; and
   (e) performing a first thermal therapy on the eyelid using the distal working end of the first type of pre-heated thermal therapy instrument.

2. The method of claim 1, further comprising exchanging the first type of thermal therapy instrument in the handheld device for a second type of thermal therapy instrument, and performing a second thermal therapy on the eyelid using the distal working end of the second type of pre-heated thermal therapy instrument without charging the battery of the handheld device.

3. The method of claim 2, further comprising exchanging the second type of thermal therapy instrument in the handheld device for a third type of thermal therapy instrument, and performing a third thermal therapy on the eyelid using the distal working end of the third type of pre-heated thermal therapy instrument without charging the battery of the handheld device.

4. The method of claim 3, wherein the first type of thermal therapy instrument is a massage instrument, and the second type of thermal therapy instrument is one type selected from the group comprising a debriding instrument and an expression instrument.

5. The method of claim 3, wherein the performing steps by each of the first, second, and third type of thermal therapy instruments are at least 2-6 minutes, and wherein the handheld device maintains each of the distal working ends of the respective thermal therapy instruments at a treatment temperature of at least 40 degrees C.

6. The method of claim 1, wherein the thermally conductive insert is tubular-shaped.

7. The method of claim 1, wherein each port is fitted with an insert to receive an instrument base portion.

8. The method of claim 1, wherein the hole in the insert is key-shaped.

9. The method of claim 1, further comprising providing the heater, and wherein the heater comprises 4-10 ports.

10. The method of claim 1, wherein the plurality of types of thermal therapy instruments includes a massage instrument having an atraumatic planar face, a debriding instrument having a hockey stick-shaped tip, and an expression instrument with pivotable jaws for clamping the eyelid.

11. The method of claim 1, further comprising providing the insert, and wherein the insert comprises a rim that engages a planar surface of the heater when the insert is inserted into one of the ports.

12. A method for heating instruments for thermal therapy comprising:
inserting a tubular-shaped insert into a heater port of a heater;
inserting a base portion of an instrument into a cavity in the insert,
activating the heater to pre-heat the instrument; and
exchanging an instrument previously-installed in a handheld device with the pre-heated instrument in the heater, without charging the handheld device.

13. The method of claim 12, further comprising performing thermal therapy on an eyelid using a distal working end of the pre-heated thermal therapy instrument.

14. The method of claim 12, wherein the cavity in the insert is key-shaped.

15. The method of claim 14, further comprising providing the insert, and wherein the insert comprises a rim that engages a planar surface of the heater when the insert is inserted into one of the ports.

16. A non-invasive thermal-based eyelid treatment method comprising:
(a) providing a plurality of types of thermal therapy instruments having a key-shaped base portion, and wherein each type of thermal therapy instrument comprises a unique distal working end;
(b) providing a battery-powered handheld device, the handheld device comprising a handle and a distal socket adapted to detachably engage the base portion of each type of thermal therapy instrument, and adapted to dynamically control heat to the distal working end of an installed thermal therapy instrument through thermal conduction;
(c) pre-heating at least one thermal therapy instrument, wherein the pre-heating is performed by an electric heater including a plurality of heated ports, and wherein each port is adapted to receive and engage the key-shaped base portion of one of said plurality of thermal therapy instruments, and during the pre-heating step, heat is transferred from the port to the one thermal therapy instrument engaged in the port;
(d) installing one pre-heated thermal therapy instrument of the pre-heated thermal therapy instruments in the handheld device; and
(e) performing thermal therapy on the eyelid using the distal working end of the pre-heated thermal therapy instrument.

17. The method of claim 16, further comprising providing an insert, and wherein each port cooperates with the insert to receive the insert, and wherein the insert comprises a key-shaped hole to receive and engage the key-shaped base portion of the thermal therapy instrument.

18. The method of claim 17, wherein the insert comprises a rim that engages a planar surface of the heater when the insert is inserted into one of the ports.

19. The method of claim 16, wherein the handheld device maintains the distal working end of the installed one thermal therapy instrument at a treatment temperature for providing the therapy, and the method further comprises, prior to the step of installing, overheating the at least one thermal therapy instrument to a pre-cursor temperature greater than the treatment temperature.

20. The method of claim 16, further comprising providing the heater.

* * * * *